United States Patent [19]

Watanabe et al.

[11] Patent Number: 5,232,855
[45] Date of Patent: Aug. 3, 1993

[54] APPARATUS FOR USE IN A AXENIC MASS CULTURE

[75] Inventors: Masataka Watanabe; Kunio Kohata, both of Tsukuba, Japan

[73] Assignee: National Institute for Environmental Studies, Ibaragi, Japan

[21] Appl. No.: 947,845

[22] Filed: Sep. 21, 1992

Related U.S. Application Data

[60] Continuation of Ser. No. 544,219, Jun. 18, 1990, abandoned, which is a division of Ser. No. 310,681, Feb. 15, 1989, abandoned.

[30] Foreign Application Priority Data

Feb. 19, 1988 [JP] Japan .................. 63-36780

[51] Int. Cl.$^5$ .................... C12M 3/00; C12M 3/06
[52] U.S. Cl. .................... 435/284; 435/311; 435/313; 362/101; 362/805; 47/1.4; 47/59; 47/60; 47/62

[58] Field of Search ................ 435/284-287, 435/299, 311, 313-316, 257, 813; 47/1.4, 1.401, 1.402, 1.405, 1.409, 59-61, 17, 17 RL; 362/805, 101

[56] References Cited

U.S. PATENT DOCUMENTS

| | | | |
|---|---|---|---|
| 3,546,812 | 12/1970 | Kobayashi et al. | 47/1.4 |
| 3,598,726 | 8/1971 | Welch | 47/1.4 |
| 4,044,500 | 8/1977 | Hitzman | 47/1.4 |
| 4,324,068 | 4/1982 | Anthony | 47/1.4 |
| 4,555,864 | 12/1985 | Mori | 47/1.4 |
| 4,952,511 | 8/1990 | Radmer | 47/1.4 |

Primary Examiner—Michael G. Wityshyn
Assistant Examiner—William H. Beisner
Attorney, Agent, or Firm—Wenderoth, Lind & Ponack

[57] ABSTRACT

The present invention provides an axenic mass culture apparatus comprising a light source for illuminating an entire surface of a culture liquid in a culture tank. According to the present invention, it is possible to achieve a light-illuminating type high-speed axenic mass culture of biotic cells.

8 Claims, 3 Drawing Sheets

APPARATUS FOR USE IN A AXENIC MASS CULTURE

This application is a continuation of now abandoned U.S. Ser. No. 07/544,219 filed on Jun. 18, 1990 which was a divisional application of now abandoned U.S. Ser. No. 07/310,681, filed Feb. 15, 1989.

FIELD OF THE INVENTION

The present invention relates to a method for an axenic mass culture and an apparatus for the application thereof. More particularly, the present invention relates to an apparatus and a method permitting high-speed mass culture of cells, that provide a highly efficient axenic culture apparatus useful as an experimental apparatus or a production equipment at a research organization or a plant and a method for axenic culture using such an apparatus.

DESCRIPTION OF THE PRIOR ART

Along with the progress of biological engineering, experimental biology and cell culture technology, there is an increasing demand for the establishment of technology for culturing biotic cells in large quantities at a high efficiency.

As to mass culture of biotic cells, it has so far been believed to be very difficult to maintain stable conditions for survivorship and growth of organisms in a relatively large scale. The reasons for this included the fact that the survival and growth mechanisms of organisms and cells have not as yet been clarified, and there has not been sufficient progress of the development of an apparatus or a system applicable for studying these mechanisms stably and in a relatively large scale under optimum conditions.

For example, in the area of research on the biotic mechanism of the occurrence of red tides studied by the present inventor, it has been difficult to conduct proper prediction or prevention of the occurrence of red tides under natural conditions for the lack of an equipment system for mass culture at a high speed. Research on red tides was carried out in respect to the abnormal growth of *Heterosigma akashiwo* and *Chattonella antiqua* often observed in the Seto Inland Sea. It is however difficult to predict such abnormal growth in actual waters from the results of laboratory experiments or studies by use of flasks in bench scale procedures, because in actual sea waters, the intensity of illumination, temperature, nutrient concentration, and other conditions vary largely, and algae causing red tides migrate in the vertical direction. In order to clarify the mechanism of the occurrence of red tides along with these changes and vertical migration, it has been absolutely necessary to establish a culture system permitting formation of an environment closer to natural conditions as to environmental factors, having an appropriate spatial expanse.

These circumstances are not limited to the case of research on red tides. In culture of biotic cells, there has been a demand for an apparatus or a system for efficiently culturing cells in a larger scale for purposes of various experimental studies and production of useful materials.

SUMMARY OF THE INVENTION

The present invention was developed in view of the circumstances as described above and has an object to provide a novel high-speed mass culture apparatus permitting efficient and high-speed culture, overcoming the problems in the conventional culture systems, and having a larger spatial scale, and a axenic culture method using such an apparatus.

The method for axenic mass culture of the present invention is characterized, for the achievement of the above-mentioned object, by irradiating light over the entire liquid surface in the culture tank, axenic inoculating algae and bacteria, and continuously performing pure axenic culturins and axenic collection.

DETAILED DESCRIPTION OF THE INVENTION

The method of the present invention and the apparatus for the application thereof are largely characterized by applying light irradiation over the entire liquid surface in the culture tank, and the incorporation of this feature as part of the whole system of the apparatus permits high-speed culture of biotic cells in large quantities.

The method of culture of the present invention and the apparatus for the application thereof are described with reference to drawings.

Figure 1:
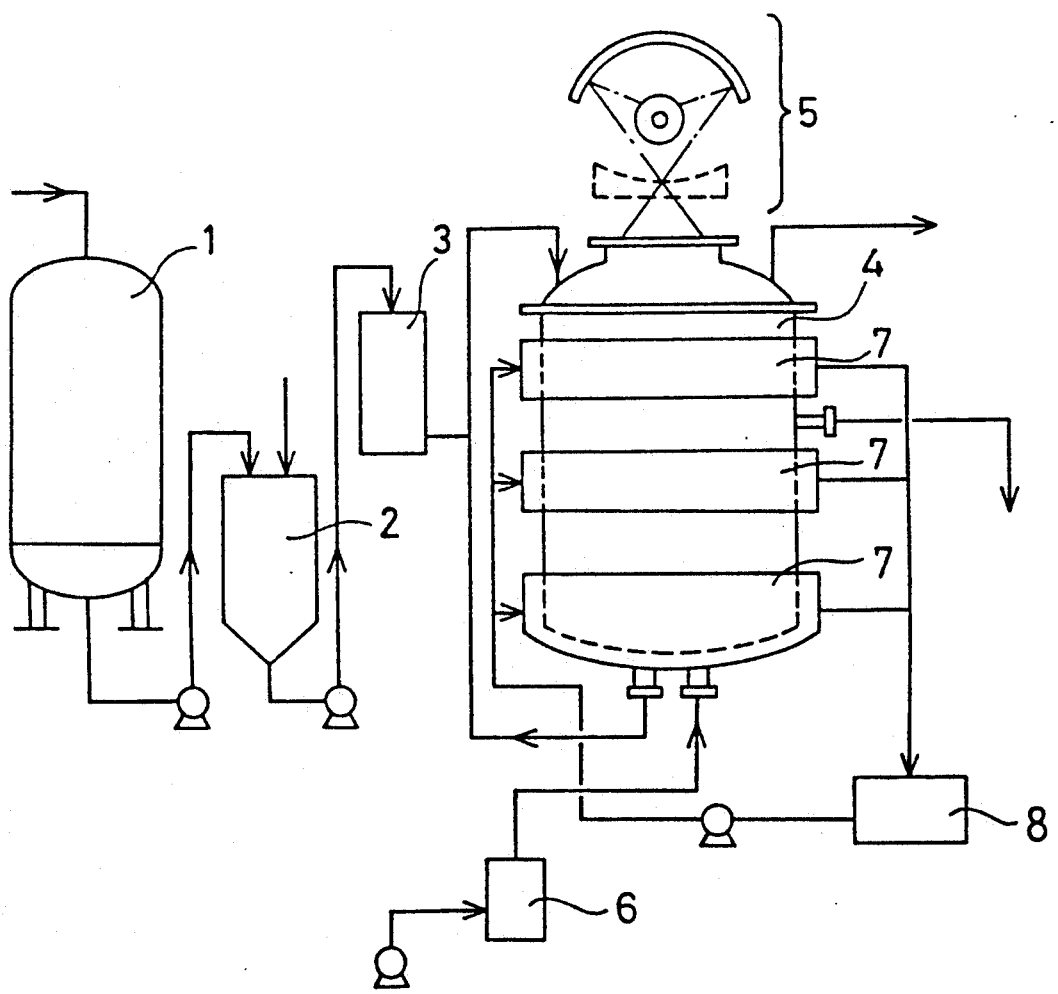
FIG. 1 is a block diagram illustrating an embodiment of the present invention.

FIG. 1 is a block diagram illustrating an embodiment of the present invention. In this embodiment, the culture apparatus has a storage tank (1) for storing a mother liquid for culturing, a mixing tank (2) for the addition of additives, a sterilizing filter (3), a culture tank (4), and a light illuminating section (5).

The culture tank (4) is equipped with a sterilizing filter (6) for air supply, a liquid temperature adjusting jacket (7), and a liquid temperature adjusting bath (8). It is important to ensure proper steam sterilization in the sterilizing filter (6) assembly and between this filter (6) and the culture tank (4).

Figure 2:
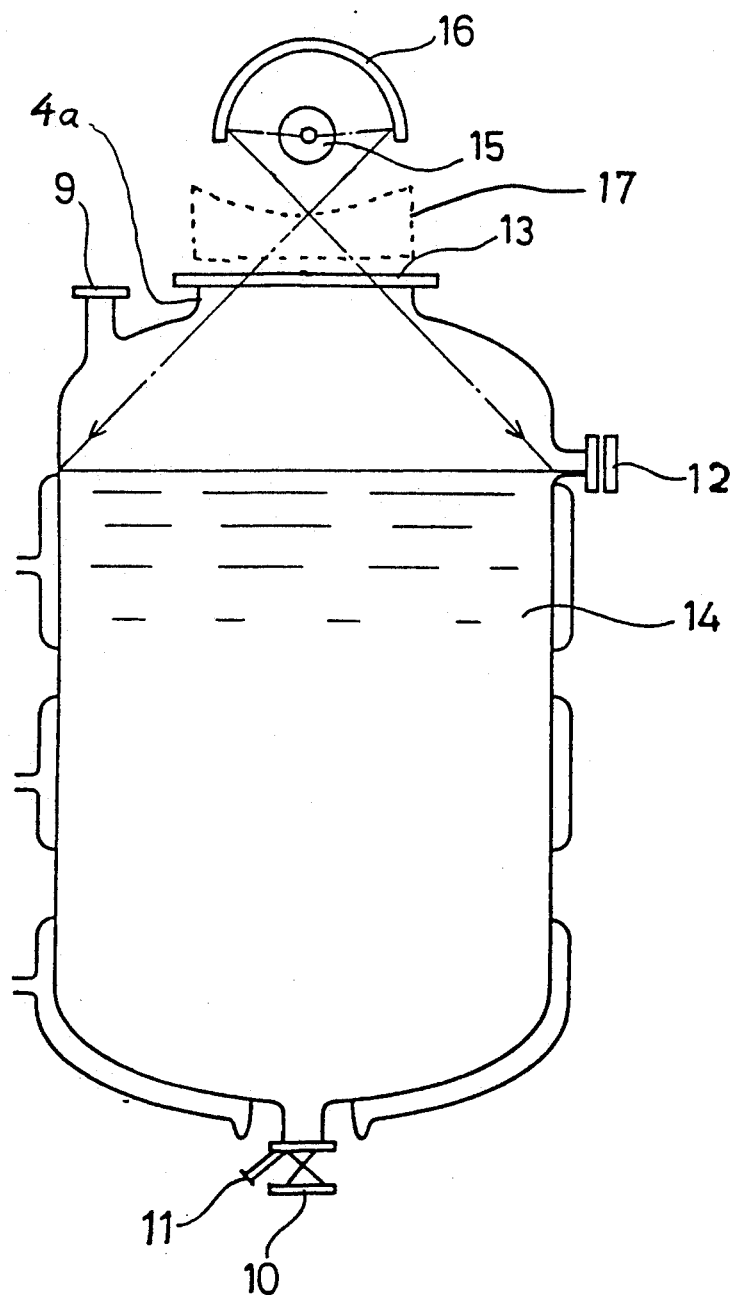
FIG. 2 is a sectional view illustrating a culture tank and an illuminating section.

FIG. 2 gives an enlarged view of the culture tank (4) and the illuminating section (5). As shown in FIG. 2, the liquid temperature adjusting jacket (7) is fitted to the culture tank (4) which has in addition an inlet port (9) of culture liquid, an air inlet port (10), an exit port (11) for recirculation of the culture liquid, and an overflow port (12) of the culture liquid, and is further provided with such means as a flow meter, a thermometer, a manometer and a biotic cell sampler for the measurement of the state of culture.

The upper opening (or irradiation opening) 4a of the culture tank is provided with glass windows (13) through which light can be irradiated onto the entire surface of the culture liquid (14). Irradiation is accomplished by means of a light source (15), a full reflecting mirror (16), and as required, a concave lens (17) for expanding the light.

The entire liquid surface can always be illuminated in response to the size of the glass windows by adjusting the distance between the light source (15) and the full reflecting mirror (16), and also adjusting the distance between the light source (15) and the concave lens (17), and that from the glass windows (13). In the preferred embodiment, the size (or area) of the irradiation opening is substantially smaller than the surface area of the culture liquid 14 contained in the culture tank (which, of course, corresponds to the horizontal cross-sectional area of the culture tank), as shown in FIG. 2.

The liquid surface may be partly illuminated, as required, through adjustment as described above.

It is needless to mention that the culture apparatus of the present invention is not limited to the examples presented above. The shape and the structure of the culture tank and the configuration of the culture system as a whole may be appropriately selected in accordance with the particular organism to be cultured. A light source and a full reflecting mirror therebehind are not always necessary, whereas a light illuminating section for irradiating light over the entire liquid surface is essential for the method and the apparatus for culture of the present invention to achieve high-speed culture in a large quantity.

As the light source composing the illuminating section, any of a mercury lamp, a halogen lamp, a xenon lamp and the like may appropriately be adopted. Natural light sent through an optical fiber is also applicable. The inner surface of the culture tank may be lined with glass, an alloy, a metal such as titanium, or a plastics such as TEFLON, depending upon the culture system to be employed.

Now, the culture apparatus of the present invention is described by means of a case where the apparatus is applied for culture of algae for the purpose of clarifying the mechanism of occurrence of red tides.

Culture apparatus

Sea water is stored in the storage tank (i) (capacity: 10 m$^3$, inner surface lined with glass) of the apparatus having the configuration as shown in FIGS. 1 and 2. The stored sea water is mixed with nutrients such as nitric acid, phosphoric acid and vitamins in the mixing tank (capacity: 0.2 m$^3$).

Culture liquid is introduced through the sterilizing filter (3) into the culture tank (4). As the sterilizing filter (3), a 5 μm Rogard filter, a 0.22 μm Milligardfilter, or a 0.22 μm Millidisk (made by Millpore Co.) is used. The culture tank (4) has a height of 2 m, an inside diameter of 1 m, and a culture medium capacity of 1 m$^3$, and an air layer of 0.4 m$^3$ may be left in the upper portion of the tank.

The pipe between the culture tank (4) and the sterilizing filter (3) may be made of TEFLON or may be lined with TEFLON on the inner surface thereof to ensure a sufficient resistance to steam sterilization and corrosion.

The culture tank (4), the sterilizing filter (3), the air filter (6) and the pipes may be steam-sterilized for 30 minutes to one hour before use. Conditions including, for example, a temperature of about 110° C. and a pressure of 0.5 kg/cm$^2$ is adopted.

The glass window (13) on the upper surface of the culture tank (4) has a diameter of, for example, 30 cm, and illumination of a 150 Å xenon lamp is projected from above. This gives conditions close to those of the sunlight in a summer daytime, with a wave length within the range of from 400 to 700 nm. The intensity of illumination in the tank in this case is about 1/5 to ⅓ that of the sunlight in a summer daytime.

The temperature of water in the culture tank (4) is adjusted by the liquid temperature adjusting jacket (having, for example, a height of 35 cm and a thickness of 5 cm) fitted to outside the tank by means of water flowing at a rate of from 2 to 6 l/minutes so that a maximum value of temperature difference between the surface and bottom layers is stably kept at about 15° C.

Measurements in the culture tank may be automatically accomplished from a data logger controlled by a microcomputer and a sequence program. The water temperature can be measured with a platinum temperature measuring resistance.

Culture conditions

*Heterosigma akashiwo* which is the species often causing red tides in Osaka Bay is cultured in the above-mentioned culture tank. Conditions are for example as follows:

Air-exposure mixing method
L/D: 12/12 cycle
Culture temperature: 20°±2° C.
f/2 culture medium (+P1.5 μmol/l)

Result of culture

Figure 3:
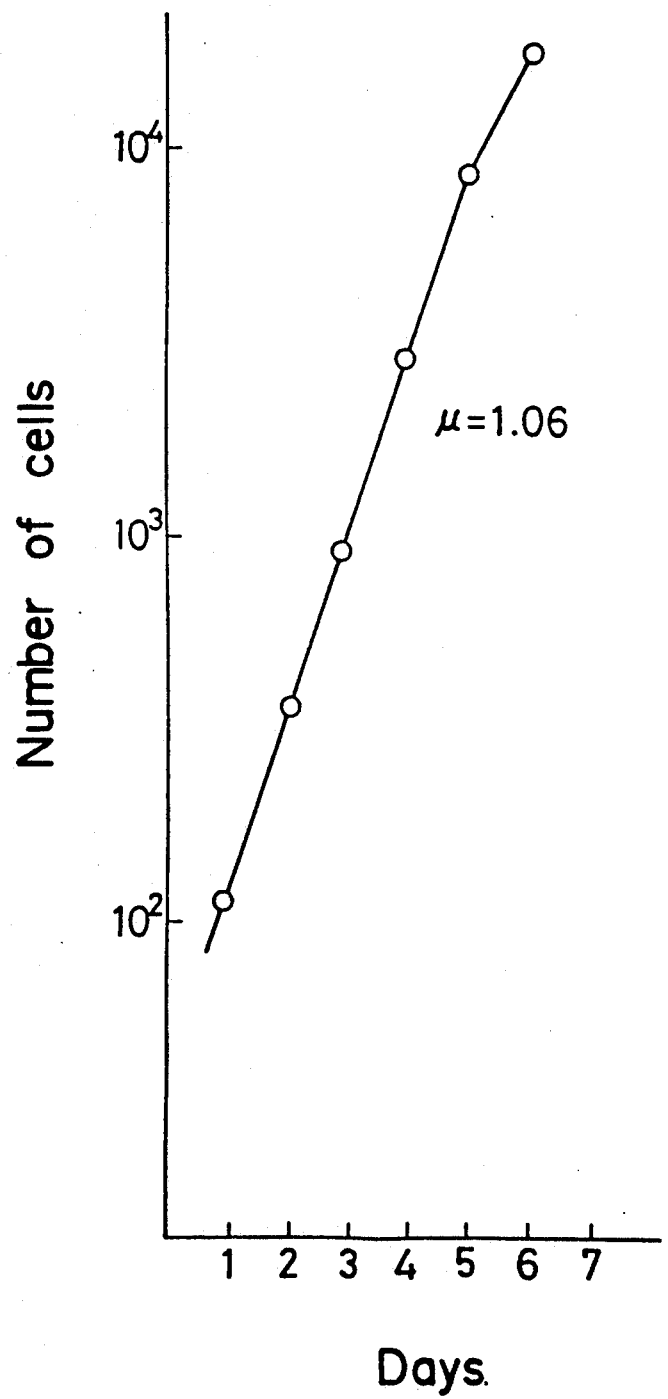
FIG. 3 is a graph illustrating the relationship between the cell concentration and time, which shows the result of culture of *Heterosigma akashiwo*.

The result of cell growth in the culture conducted in the apparatus under the conditions as mentioned above is shown in FIG. 3. FIG. 3 suggests that cells rapidly grow within a very short period of time. The result showed a specific growth rate $\mu(d^{-1})$, i.e., a cell concentration per unit measureing time (number of cells·l$^{-1}$) of 1.06.

Because, in a conventional irradiated culture tank of substantially the same scale, this specific growth rate $\mu$ is about 0.4 d$^{-1}$, that available in the method and the apparatus of the present invention far exceeds the past highest level. High-speed culture in a large quantity is thus achieved.

This result demonstrates that the illuminating method of the present invention, acting synergetically with stability of the temperature gradient in the vertical direction of the culture tank and other features, form a very excellent culture environment.

According to the present invention, as described above in detail, it is possible to conduct high-speed culturing in a large quantity, and a method and an apparatus for the application thereof for high-speed axenic culture of the illuminating type, which is very useful as an experimental apparatus and a production equipment are achieved.

What is claimed is:

1. An axenic mass culture apparatus comprising:
   a culture tank pretreated by steam-sterilization, having an irradiation opening at a top end thereof, having a horizontal cross-sectional shape with a predetermined area, and being adapted to contain a culture liquid with a surface area corresponding to said predetermined area;
   a glass window covering said irradiation opening;
   a light source mounted above said glass window;
   wherein said irradiation opening of said culture tank is substantially smaller in area than said predetermined area of said horizontal cross-sectional shape of said culture tank; and
   wherein a means is provided for causing said light source to irradiate, through said irradiation opening, an entirety of the surface area of a culture liquid contained in said culture tank.

2. An axenic mass culture apparatus as recited in claim 1, wherein
   said means comprises a full reflecting mirror mounted above said light source and partially surrounding said light source.

3. An axenic mass culture apparatus as recited in claim 2, wherein
said means further comprises a concave lens mounted between said light source and said irradiation opening.

4. An axenic mass culture apparatus as recited in claim 1, wherein
said light source comprises a xenon lamp.

5. An axenic mass culture apparatus as recited in claim 1, wherein
said light source comprises an optical fiber.

6. An axenic mass culture apparatus as recited in claim 1, wherein
said culture tank includes a culture liquid inlet port and an air inlet port;
a first sterilizing filter is provided for filtering the culture liquid being introduced into said culture liquid inlet port; and
a second sterilizing filter is provided for filtering air being introduced into said air inlet port.

7. An axenic mass culture apparatus as recited in claim 1, further comprising
a lining provided on an inner surface of said culture tank.

8. An axenic mass culture apparatus as recited in claim 1, wherein
said light source is a single light source;
said irradiation opening is a single irradiation opening; and
said means is operable for causing said single light source to irradiate, through said single irradiation opening, the entirety of the surface area of the culture liquid contained in said culture tank.

* * * * *